United States Patent [19]

Rich et al.

[11] 4,062,746

[45] Dec. 13, 1977

[54] SOLID PHASE SYNTHESIS OF PROTECTED PEPTIDES

[75] Inventors: Daniel H. Rich, Madison, Wis.; Sweet K. Gurwara, Williamsville, N.Y.

[73] Assignee: Wisconsin Alumni Research Foundation, Madison, Wis.

[21] Appl. No.: 575,478

[22] Filed: May 7, 1975

[51] Int. Cl.$^2$ ............................................. C08L 81/00
[52] U.S. Cl. ............................... 204/159.12; 204/1 R; 204/160.1; 260/8; 260/78 A; 260/112.5 R; 526/52; 260/6; 260/7
[58] Field of Search ................. 260/78 A, 112.5 R, 6, 260/7, 8; 204/1, 159.12, 160.1; 526/52

[56] References Cited

U.S. PATENT DOCUMENTS

| | | | |
|---|---|---|---|
| 3,573,253 | 3/1971 | Gray | 260/112.5 R |
| 3,645,996 | 2/1972 | Southard | 260/112.5 R |
| 3,700,609 | 10/1972 | Tregear et al. | 260/112.5 R |
| 3,775,378 | 11/1973 | Dahimans et al. | 260/112.5 R |
| 3,784,523 | 1/1974 | Loffet | 260/112.5 R |
| 3,814,732 | 6/1974 | Wang | 260/112.5 R |

OTHER PUBLICATIONS

Rich et al., Chem. Comm., 1973, 610–611.
Barltrop et al., Chem. Comm., 1966, 822–823.

*Primary Examiner*—Delbert R. Phillips
*Attorney, Agent, or Firm*—McDougall, Hersh & Scott

[57] ABSTRACT

The invention is addressed to the preparation of 3-nitro-4-bromomethyl benzoic acid, as a new compound from which 3-nitro-4-bromomethyl benzoyl amide polystyrene resin can be prepared for solid synthesis of protected peptide acids and amides and separation thereof without cleavage of acid labile protecting groups or decomposition of aromatic acid groups and from which purified polypeptides can be formed.

4 Claims, No Drawings

SOLID PHASE SYNTHESIS OF PROTECTED PEPTIDES

This invention relates to the preparation of polypeptides by solid phase synthesis wherein 3-nitro-4-amino methyl benzoyl amide resin and 3-nitro-4-bromomethyl benzoyl amide resin are prepared from 3-nitro-4-bromomethyl benzoic acid, and from which the protected peptide acids or amides can be removed by photolysis in high yield, without destroying acid base labile protected groups or aromatic amino acids.

The C-terminal amide group is present in several biologically active peptides. Such peptides have been synthesized by solid phase methods (R. B. Merrifield, J. Am. Chem. Soc. 85 2149 (1963), in which the C-terminal amide of the protected peptide was removed from the resin by aminolysis or by transesterification (H. C. Beyerman, H. Hindricks and E. W. B. deLeer, J.C.S. Chem. Comm. 1668 (1968). However, these conditions necessitate the use of side chain ester protecting groups which are resistant to aminolysis or transesterification and therefore restrict the type of acid labile protecting groups that can be used to synthesize the peptides. Furthermore, peptides with hindered C-terminal residues such as valine in secretin, can be difficult to remove from the resin. Thus new and improved methods for preparation and removal of protected peptides from a solid phase, as the C-terminal amide, is desirable.

The solid phase method of peptide synthesis introduced by Merrifield (supra) is an effective method for the rapid synthesis of peptide. However, the products prepared by this method are often difficult to purify. Impurities, such as failure sequences caused by changes in the physical-chemical properties of the polymer, accumulate during stepwise synthesis and can be difficult to remove. It has been suggested that a more homogeneous final product might be isolated by coupling pure protected peptide fragments onto the solid support. Failure sequences formed during synthesis, using fragment coupling, would differ substantially from the desired product and would be more readily removed by purification. If the fragment coupling is to become generally useful, a convenient method for preparing protected peptide acids and amides, such as Boc-peptide acids and amides, is needed. As described, these derivatives have been prepared by solid phase synthesis but either transesterification or hydrazinolysis reactions were required to remove the Boc-protected peptides from the resin.

It is an object of this invention to provide a method whereby protected peptide acids and amides can be removed by photolysis under conditions which do not destroy aromatic residues, or cleave acid or base labile protected groups, and it is a related object to produce and to provide methods for producing new intermediates for use in the same as well as new and improved polypeptides which result from same.

We have succeeded in the removal of protected amino acids and peptides by photolysis from ortho-nitro chloromethyl polystyrene resins, as reported in J. Chem. Soc. Chem. Comm. 610–11 (1973). Using this method, the purified protected tripeptide Boc-Ser (Bzl)-Tyr (Bzl) -Gly

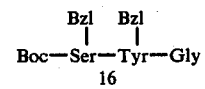

was obtained in 62% yield, based on starting Boc-Glycin resin. However, by this method, the synthesis of longer peptides was not successful.

By continuation of the investigation, we have found that the deficiencies can be overcome by the use of 3-nitro-4-bromomethyl benzoyl amide polystyrene resin instead of the 3-nitro-4-chloromethylated derivative. This is believed to result from the fact that the 3-nitro-4-bromo-methylated benzoyl amide polystyrene resin swells more in non-polar solvents than the more polar 3-nitro-4-chloro-methylated polystyrene resins and that the lower extent of swelling experienced by the latter reduces penetration of the solvent and rates of reaction, thereby to interfere with the preparation of longer chain protected polypeptides.

The invention will now be described with reference to the synthesis of 3-nitro-4-bromomethyl benzoyl amide resin; the synthesis by the addition of peptide onto the resin via Boc-amino acids or amides, for solid phase peptide synthesis to form polypeptides which are capable of being separated in a purified state by photolysis. The description will use, for purposes of illustration, the synthesis of protected fragments of LH-RH, but it will be understood that other polypeptides, acids and/or amides can be produced by the method described including the coupling in various combinations of Boc-amino acids or peptides including Boc-Pro, Boc-Arg (Tos), Boc-Leu, Boc-Gly, Boc-Tyr (Pzl), Boc-Ser (Bzl), Boc-Ala, Boc-Val, Boc-Ileu, Boc-Phe, Boc-Hypro, Boc-Thr (Bzl), Boc-Cys (Bzl), Boc-Met, Boc-Asp (Bzl), Boc-Glu (Bzl), Boc-Lys (Bzl) and Boc-His (Bzl).

The sequence of reactions, to be described in the following examples, for the synthesis of the 3-nitro-4-bromomethyl benzoyl amide resins may be represented by the following:

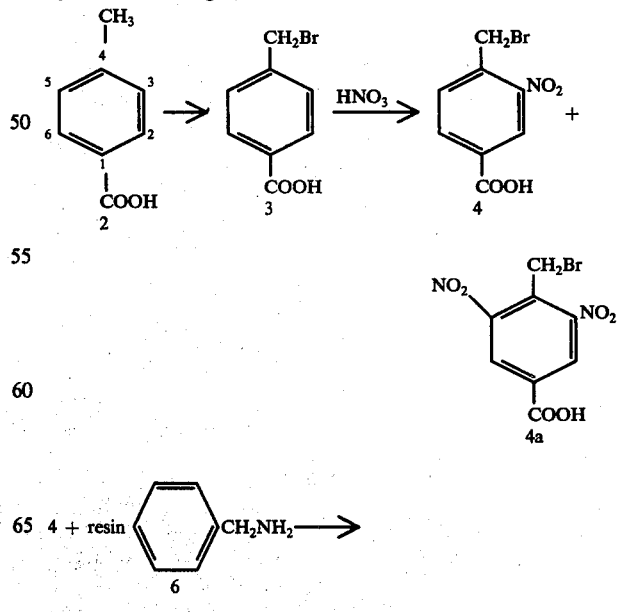

-continued

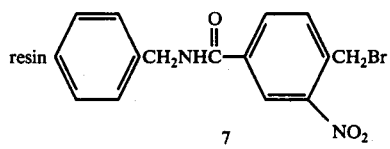

7

EXAMPLE 1

Preparation of 3-nitro-4-bromomethyl benzoic acid 4

Briefly described, p-toluic acid 2 is refluxed with N-bromo-succinimide and benzoyl peroxide in dry benzene to give α-bromo-p-toluic acid 3 which, upon reaction with nitric acid, is converted to 3-nitro-4-bromomethyl benzoic acid 4. This is believed to be a new compound and represents a parent compound in the synthesis forming the subject matter of this invention. At slightly higher temperatures, above −10° C, the corresponding dinitro derivative 4a predominates.

DETAILED PROCEDURE

Benzoyl peroxide (0.2 g) and N-bromosuccinimide (17.8 g, 100 mmol) (recrystallized from hot $H_2O$) were added to a suspension of p-toluic acid (13.6 g, 100 mmol) (recrystallized from $CHCl_3$/MeOH) in dry benzene (100 ml). The mixture was heated at reflux for 24 hours. Removal of the solvent in vacuo gave a white residue which was suspended in 100 ml of boiling $H_2O$, collected by filtration and washed with boiling $H_2O$ (4 × 100 ml). The crude product was dried and recrystallized from hot MeOH to give pure acid (17.5 g, 81.4%); m.p. 224°–226°, i.r. (Nujol) 2800-2400, 1690 (COOH), 1560 cm$^{-1}$ (Aromatic); nmr (CDCl$_3$, DMSO-d6) δ 4.61 (s,2) 7.8 (8.4 J=8Hz), 10.4 (s, 1) UVmax (meOH) 232 mμ ($t$=1.32 × 10$^4$), 285 mμ ($t$=1166). Anal. Calcd for $C_8H_7BrO_2$: C, 44.68; H, 3.28; Br 37.15; found: C, 44.50; H, 3,18; Br, 37.02.

The bromoacid 3 (11.8 g) was added in portions over 0.5 hour to 100 ml of 90% $HNO_3$ (white fumming) at −10° C. The suspension was stirred at −10° for an additional 2 hours when the solution became clear orange. This solution was poured onto crushed ice. The product was collected by filtration, washed with ice cold $H_2O$ (3 × 50 ml) until the washings were neutral. Drying in vacuo followed by crystallization twice from $CH_2Cl_2$/hexane gave pure nitro acid 4 (11.02 g, 85%): m.p. 125–126, i.r. (Nujol) 2800-2300, 1690, 1610 (COOH), 1600 (Aromatic), 1540, 1300 cm$^{-1}$ (NO$_2$); nmr (CDCl$_3$, DMSO-d6) 4.9 (S,2), 7.8 (d,1), 8.2 (dd,1), 8.6 (d,1) 10.8 (s,1); Rf(5) 0.55; Rf (1) 0.82; UVmax (CH$_3$OH) 227 mμ ($t$ = 2.13 10$^4$) 305 mμ ($t$ 4.1 × 10$^3$).

Anal. Calcd for $C_8H_6NBrO_4$: C, 36.95; H, 2.32; N, 5.38; Br 30.73; Found C, 37.16; H, 2.46; N, 5.47; Br 30.97.

EXAMPLE 2

Preparation of 3-nitro-4-bromomethyl benzoyl polystyrene resin 7

Briefly described, the amino methyl polystyrene resin 6 is produced by reaction of the chloro methylated polystyrene resin with anhydrous ammonia in methylene chloride. Other solvents can be used but when reacted in the presence of methylene chloride, the degree of cross linking of the resin is relatively unchanged while, at higher temperatures and in the presence of different solvents, such as methanol, methanoldioxane or dimethyl formamide, while the ammonation takes place, the degree of resin cross linking is increased. Treatment of the amino resins with the nitro acids 4 and dicyclohexylcarbodiimide in dimethylformamide is followed by acetylation of the residual amino group by reaction with acetic anhydride and diisopropyl ethylamine.

DETAILED PROCEDURE

Aminomethylated polystyrene resin 6 (1.0 g 0.4 mmol NH$_2$/g) was added to a solution of the nitro-acid 4 (0.52 g, 2 mmol) and dicyclohexylcarbodiimide (DCC) (0.42 g, 2 mmol) in dimethylformamide (DMF) (10 ml). The suspension was stirred at room temperature for 18 hours and filtered. The resin was washed with MeOH, CH$_2$Cl$_2$, MeOH (3 × 20 ml for 1 minute each), dried in vacuo and placed again in a solution of 0.260 g of nitro acid 4 and 0.206 g of DCC in 10 ml DMF. After the same workup (vide supra), the resin was suspended in CH$_2$Cl$_2$ (25 ml) and acetic anhydride (0.61 g, 6 mmol) and diisopropylethylamine (0.774 g, 6 mmol) were added. The suspension was stirred at room temperature for 1 hour, washed with CH$_2$Cl$_2$, MeOH (3 × 20 ml for 1 minute) and dried in vacuo to give the desired resin 7 (1.08 g) ir (KBr) 1600 (NH$_2$), 1560, 1350 (NO$_2$) cm$^{-1}$. The resin contained 0.3 mmol/g of bromine and no free amine (Dorman)[31]; 100 mg of resin swelled to 1.0 mg in dry CH Cl$_3$.

Anal. Calcd for 0.3 mmol Br$^-$/g, 0.6 mmol N/g Br, 2.4; N 0.84; Found: Br 2.08; N 0.70.

The light yellow product contained 0.3 mmol bromine/g resin and no detectable free amino groups. The high bromine content and correct nitrogen analysis indicated that little if any alkylation of resin amino groups by bromomethyl groups had occurred. The nitro resin 7 swells in chloroform and all other solvents used in solid phase synthesis to the same extent as does the chloromethylated polystyrene starting material.

Alternatively, the bromine group on the 3-nitro-4-bromomethyl benzoic acid 4 is replaced by an amino group which is then protected by a Boc group for resin coupling in accordance with the following equation:

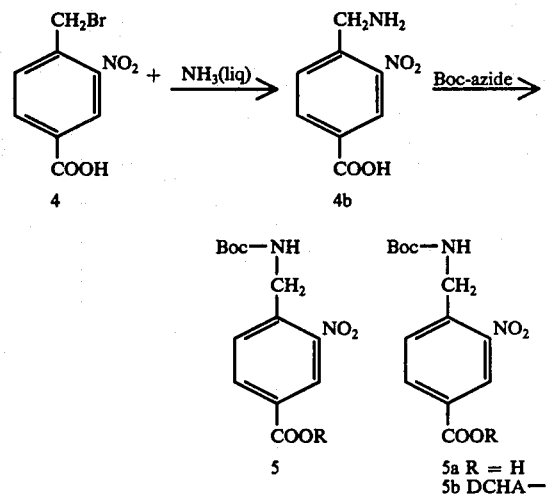

Compound 5, which is also believed to be new, reacts in the same way with the methylamino resin (6) to produce the Boc protected derivative in accordance with the following equation:

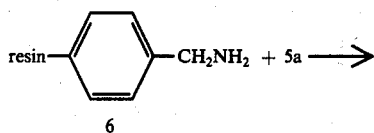

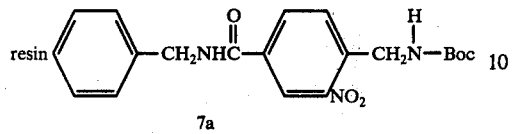

EXAMPLE 3

Preparation of 3-nitro-4-aminomethyl benzoic acid 4b

Dry liquid ammonia (15 ml) was added to 2.0 g (7.7 mmol) of 3-nitro-4-bromomethyl benzoic acid 4 in a pressure resistant bottle. The solution was stirred at 0°–5° for 24 hours. The bottle was then cooled to −78° C, opened and the ammonia evaporated. The residue was suspended in methanol, collected by filtration, washed with methanol and dried to give acid 4b: m.p. 235°–237° C, yield 1.089 g (72%).

EXAMPLE 4

Preparation of 3-nitro-4-t-butoxycarbonyl (Boc) aminomethyl benzoic acid 5a

Triethylamine (0.3 ml, 2 mmol) and tert-butyl oxycarbonyl azide (0.15 ml, 1 mmol), were added to a solution of acid 4b (0.196 g, 1 mmol) in dimethylsulfoxide (6 ml). The reaction mixture was stirred at 25° C for 18 hours. The solution was diluted with water (10 ml) and washed with ether (10 ml). The aqueous layer was cooled to 0° C and solid citric acid was added until the pH was between 2 and 3. The solution was washed three times with ethyl acetate, the ethyl acetate layers were dried and evaporated to dryness in vacuo to give acid 5a. Acid 5a was dissolved in methylene chloride (5 ml) to which was added an etheral solution of dicyclohexylamine (1 ml/3 ml ether). The salt 5b was crystallized from ether to give pure 5b: 0.4 g, 85%; m.p. 205°–207° C.

Anal. Calculated for $C_{25}H_{39}N_3O_6$: C 62.87, H 8.23, N 8.80. Found: C, 62.61, H 8.46 and N 8.55.

EXAMPLE 5

Preparation of 3-nitro-4-t-butoxycarbonyl (Boc) aminomethyl benzoyl amide resin 7a To a solution of acid 5a (0.889 g, 3 mmol) in 10 ml DMF, was added 0.609 g (3 mmol) DCC in 10 ml DMF. The amino resin 5 g, 0.3 mmol $NH_2$/g) was added to the solution and the suspension stirred for 18 hours. The resin was filtered, washed three times with 20 ml portions each of DMF, methanol, methylene chloride, methanol before drying in vacuo to yield resin 7a: 0.3 mmol amine group/g resin after the t-Boc group is removed.

It will be apparent from the above that the term "Boc", as used herein, refers to t-butoxycarbonyl protective group. Other protective groups, well known to the art, may be used instead of the t-butoxycarbonyl (BOC) groups for protection of the peptide acids and amides.

Similarly, starting with the resin represented by the compound 7a, polypeptides, such as the C-terminal peptide amide LH-RH can be produced by solid phase synthesis, followed by removal of the purified protected polypeptide by photolysis, in accordance with the following equations:

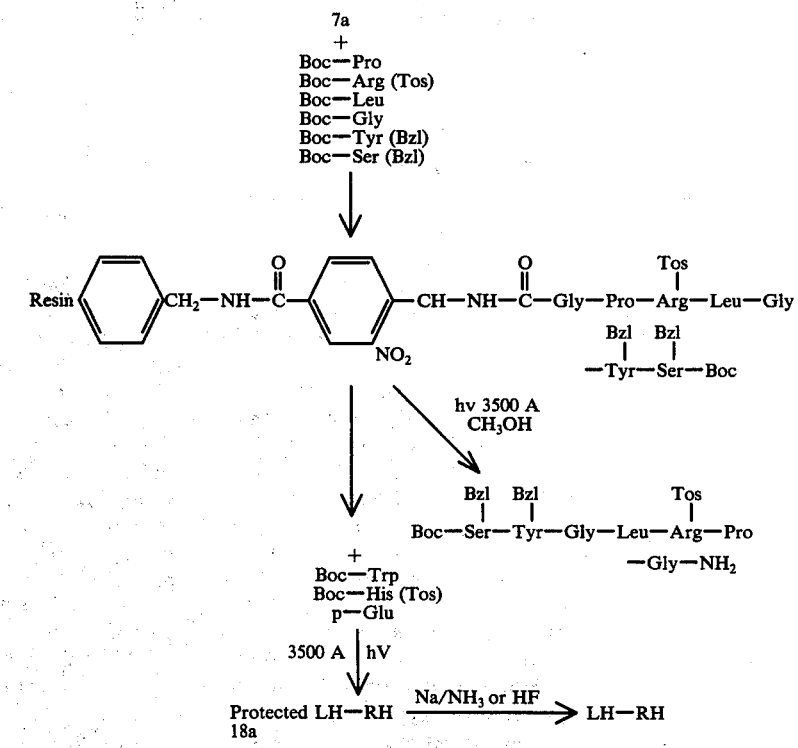

The attachment of one or more Boc amino acids to the resins 7 or 7a by solid phase synthesis and release of the fragment from the resin by photolysis are represented by the following equations:

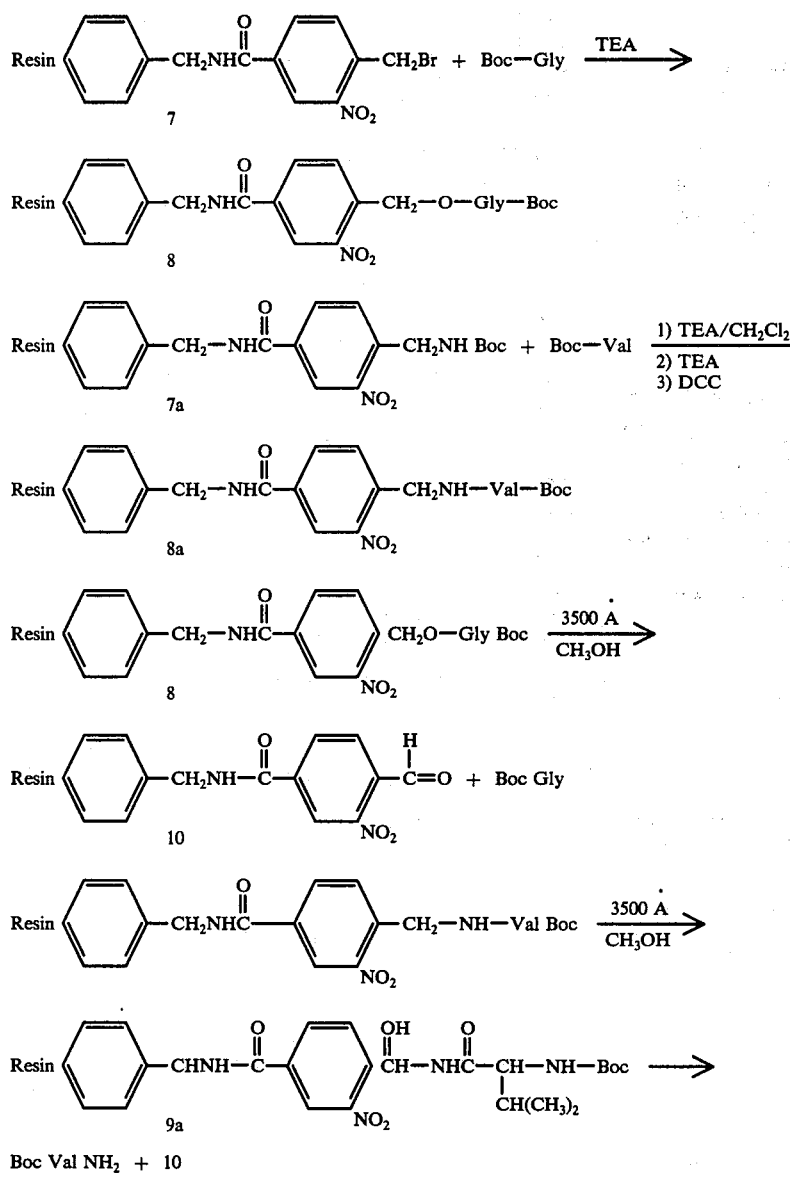

The compound 9a is believed to exist as an intermediate that is formed in response to irradiation of the Boc protected amino (peptide) resin.

The attachment of the Boc-amino acid to the nitro resin 7 is effected by heating under reflux with triethylamine (TEA) or preferably with diisopropylethylamine, in ethyl acetate. Less quaternization of the resin is experienced with the use of diisopropylethylamine. No racemization has been detected either during attachment or during photo-chemical removal of the amino acid derivative by photolysis. Boc-amino acids are attached to resin 7a using a suitable coupling reagent such as DCC.

The Boc-amino acids and peptides are released from the resin 7 or 7a by photolysis in methanol or other short chained $C_1$ to $C_5$ alcohol, under anaerobic conditions, preferably in the absence of oxygen which has the tendency to reduce yield as well as purity of the product.

In accordance with the practice of this invention, any number or any combination of amino acids or amides (peptides) can be attached to the resins 7 or 7a by solid phase synthesis, such as described for the attachment of a single Boc protected amino acid or amide to the resin, and then the combination of multiple amino acids or amides, in block arrangement, or in any arrangement or number desired, can be removed from the resin by the described method of photolysis to produce the formed polypeptide. With the Boc group or other protective group present, multiple polypeptides, such as in combinations of 10 + 10 + 10 + 10 can be joined with subsequent separation of the combination from the resin for photolysis to produce purified tailor-made enzymes of the type which have been the subject of extensive research by the most highly skilled in the art.

The example: Boc peptide chains of 10 amino acids can be split off by photolysis from the resin, in accordance with the practice of this invention, for subsequent addition by the described solid phase synthesis into a compound 7a or 8 with 10 or more protected amino acids to produce a purified Boc protected polypeptide chain of some 20 peptides. Upon separation by photolysis, this chain can be added for combination with another resin chain whereby 10, 20, 30, 40, 50 and more amino acids or amides of various types and in various combinations can be produced in a purified form upon separation by photolysis from the nitro resin.
The following equations will further illustrate the solid phase synthesis and separation by photolysis for buildup of the polypeptide chain in the manner described.
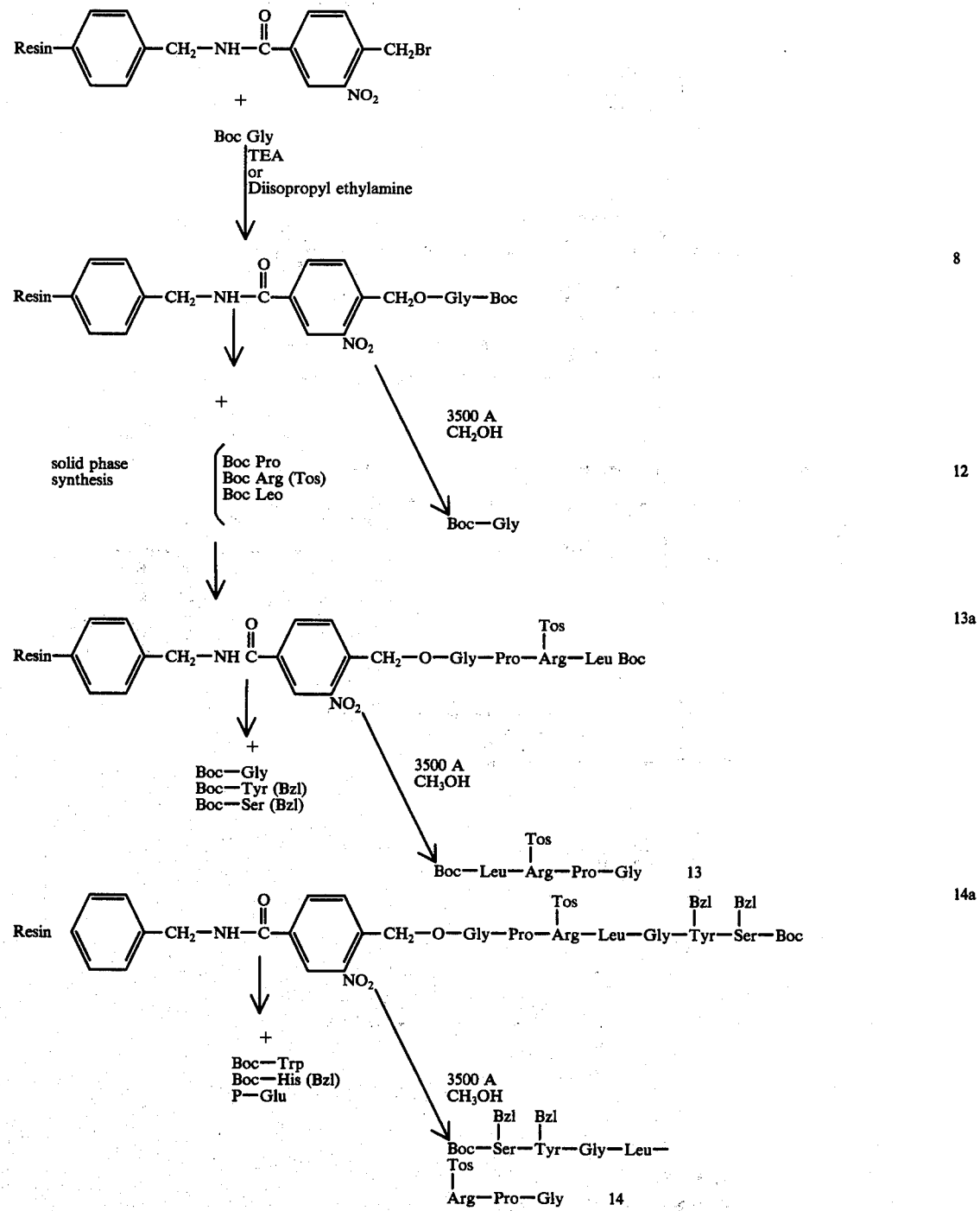

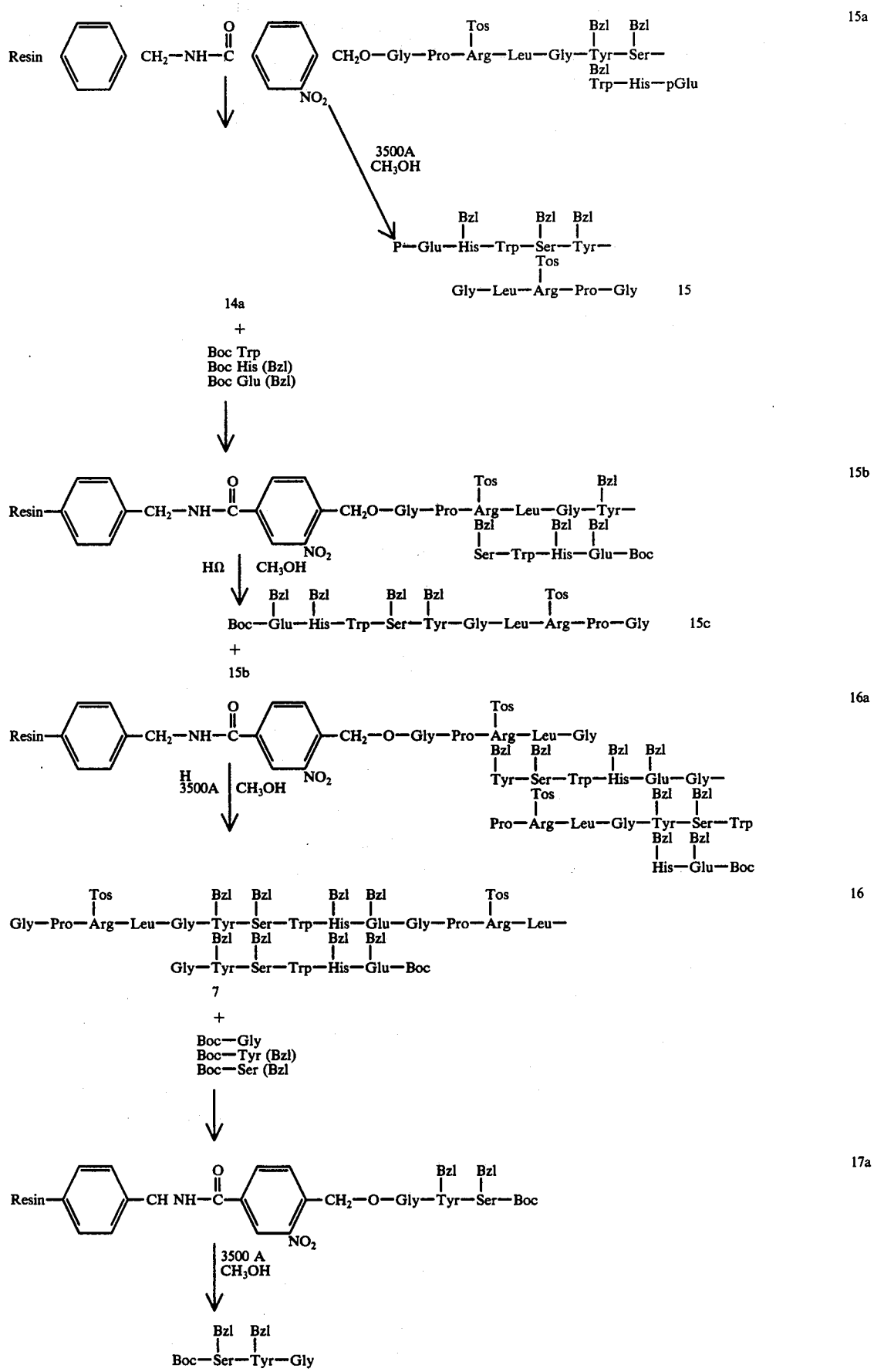

-continued

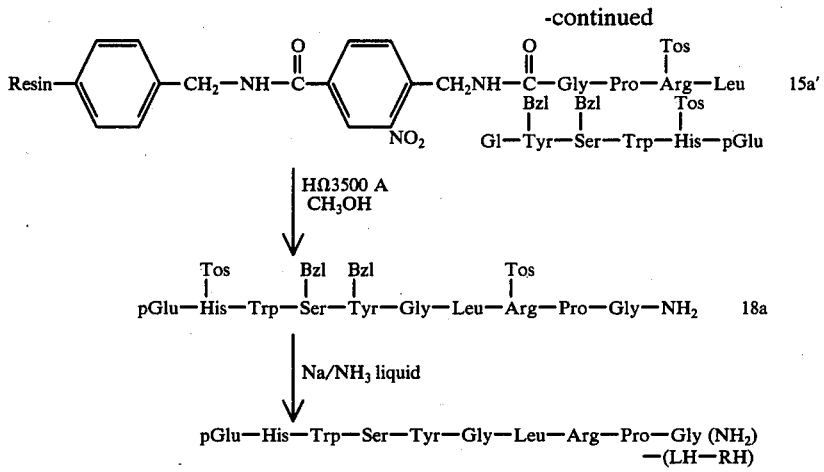

15a' is produced by the procedure illustrated by equation 15c except that 7a is used instead of 7.

The high yields of purified polypeptide isolated by photolysis indicates that the hindered amino acid derivative can be removed efficiently by photolysis under mild conditions. In addition to the Boc protective groups, the O-benzyl group on Ser, Tyr, Asp and Glu, and the Tos group on Arg and His are not removed by photolysis but can be removed from the separate hindered polypeptides by reaction with sodium in liquid ammonia, or other methods.

The preparation of polypeptides, in accordance with the procedures of this invention, by solid phase synthesis, and the separation by photolysis will now be illustrated by the following representative examples.

EXAMPLE 6

Solid phase synthesis

In general, the solid phase synthesis was carried out on a Beckman model 990 Peptide synthesizer using the following procedure: (1) deprotection was achieved by two successive washes (5 min and 30 min) of 25% TEA in $CH_2Cl_2$ which contained 1 mg/ml of indole; (2) two equivalents of each Boc-amino acid per equivalent Boc-glycine resin was used; (3) a second coupling of each amino acid in 50% $DMF/CH_2Cl_2$ was performed; (4) the resin was washed with ethanol and dried with nitrogen at the end of each synthesis.

EXAMPLE 7

Removal of protected peptides from the nitro resins

A suspension of resin in anhydrous MeOH or EtOH was placed in a flask surrounded by a jacket containing a 40% $CuSO_4$ solution. Dissolved air was removed from the suspension by passing prepurified, $O_2$ free, nitrogen for two hours through the solution which was under a slight vacuum. The suspension was then irradiated at 3500 A for 18–24 hours. Upon completion of photolysis the suspension was filtered and the resin washed three times for two minutes with 20 ml portions of each of the following solvents: EtOH, $CH_2Cl_2$, 50% $CH_2Cl_2$-EtOH, EtOH. The filtrate and washings were evaporated in vacuo. The crude product was purified by chromatography over a Sephadex LH-20 column (100 g 2.5 × 80 cm., flow rate 30 ml/hr, fraction volume of 5 ml each). The elution was monitored by a dual beam UV detector from Instrumentation Specialties Co. The products were checked for homogeneity in the following thin layer chromatograph (tlc) solvent systems: 1 (acidic), n-butanol: acetic acid: water: ethylacetate (1:1:1:1); 2 (basic), n-butanol: $NH_4OH$ (7.3); 3, n-butanol: acetic acid: water (4:1:5 upper layer); 4, chloroform: methanol (7.5:25); 5, chloroform: methanol (1:1).

Specific Examples

EXAMPLE 8

Preparation of Glycine Resin 8

The 3-nitro-4-bromomethyl resin 7 (4.0 g 0.3 mmol $Br^-/g$) was added slowly to a solution of Boc-glycine (0.70 g, 4 mmol) in 20 ml of EtOAc. Diisopropyl ethyl amine (0.52 g, 4 mmol) was added and the suspension was gently heated at reflux for 48 hours. The resin was collected by filtration, washed with EtOAc, MeOH, $CH_2Cl_2$, MeOH (3 × 25 ml for 2 minutes), and dried in vacuo to give the desired product 8 (4.2 g). The resin contained 0.3 mmol/g of Boc-Glycine and no detectable bromine (Dorman method).

EXAMPLE 9

Preparation of tetrapeptide 13

The peptide resin 13 was synthesized as described in Example 6 by adding Boc glycine resin 8 (2.0 g, 0.23 mmol glycine/g), to successive solutions of Boc-Pro, Boc-Arg (Tos) and Boc-Leu. Amino acid analysis gave $Leu_{1.0} Arg_{0.92} Pro_{0.91} Gly_{1.01}$. A suspension of 1.0 g of 13a in absolute EtOH was photolyzed and purified as described in the preceding Example 7. The purified tetrapeptide 13 was obtained in 56% (0.098 g): m.p. 122°–124°; tlc $Rf_1$ 0.93, $Rf_2$ 0.29, $Rf_3$ 0.46, $Rf_4$ 0.24; UV max (MeOH) 255 mµ ($t = 1200$); nmr was consistent with structure; amino acid analysis: $Leu_{1.04} Arg_{1.0} Pro_{1.0} Gly_{1.03}$ $[\alpha]^{27}D$ - 14 (C 1, $CH_3CO_2H$)

Anal. Calcd. for $C_{31}H_{49}N_7SO_9$; C, 53.51; H, 7.10; N, 14.09; S, 4.61 Found: C, 53.58; H, 7.20; N, 14.28; S, 4.63.

EXAMPLE 10

Preparation of heptapeptide 14

The synthesis of the peptide resin 14a was done following the method of Example 6 using Boc resin 13a (2.0 g, 0.3 mmol glycine/g). Amino acid analysis gave $Gly_{2.0}$, $Ser_{1.3}$, $Pro_{1.2}$, $Leu_{1.1}$, $Tyr_{1.4}$, $Arg_{0.8}$. A suspension of 0.5 g of 14a in absolute MeOh was photolyzed and purified as described in Example 7. The purified heptapeptide 14 was obtained in 50% yield (0.057 g): m.p. 135°–138°; tlc $Rf_1$ 0.86; $Rf_2$ 0.44; $Rf_3$ 0.87; $Rf_4$ 0.91; UV max (MeOH) 264 mµ ($t = 3300$); the nmr was consistent with the structure. The amino acid composition was $Gly_{2.0} Ser_{1.06} Pro_{0.88} Leu_{1.12} Tyr_{0.87} Arg_{0.73}, [\alpha]^{27}D$ - 12 (c 1, $CH_3CO_2H$).

Anal. Calcd for $C_{59}H_{78}N_{10}SO_{14}$: C, 59.88; H, 6.64; N, 11.84; S, 2.71. Found: C, 59.96; H, 6.64; N, 11.69; S, 2.89.

EXAMPLE 11

Preparation of decapeptide 15

The synthesis of the peptide resin 15 was done according to the method described in Example 6 by building on Boc glycine resin (2.0 g, 0.3 mmol Gly/g) or by using resin 14a and adding Boc-Trp, Boc-His (Bzl) and Pyro-Glu. Amino acid analysis gave $Gly_{2.0} Ser_{0.96} Pro_{1.05} Glu_{1.05} Leu_{1.06} Tyr_{1.13} Arg_{1.10} BzlHis_{0.86}$. A suspension of 1.1 g of 13 in absolute ethanol was photolyzed and purified as described in Example 7. The purified protected decapeptide 15 was obtained in 64% yield (0.257 g): m.p. 155°–159°; tlc $Rf_1$ 0.80, $Rf_2$ 0.11, $Rf_3$ 0.75, $Rf_4$ 0.04; UV max (MeOH) 262 mμ (t = 6000); the nmr was consistent with the structure; $[\alpha]^{27}D$ - 22 (c 1 ($CH_3CO_2H$); the amino acid composition was $Gly_{1.90} Ser_{0.92} Pro_{1.0} Leu_{1.0} Tyr_{0.92} Arg_{1.02} Glu_{1.02}$.

Anal. Calcd for $C_{83}H_{98}N_{16}SO_{16}CH_2Cl_2$: C, 59.56; H, 5.95; N, 13.23; S, 1.89. Found: C, 59.80; H, 5.44; N, 13.20; S, 1.80

EXAMPLE 12

Preparation of tripeptide 17

The peptide resin 17a was synthesized according to the procedure of Example 6 using Boc glycine resin 8 (2.0 g, 0.3 mmol Gly/g) and adding Boc Tyr(Bzl) and Boc Ser (Bzl). Amino acid analysis gave $Ser_{1.0} Tyr_{0.74} Gly_{1.26}$. A suspension of 0.5 g of 17a was photolyzed and purified as described in Example 7. The purified tripeptide 17 was obtained in 50% yield (0.045 g) and was found to be identical[1] to a sample prepared by solution procedure: m.p. 136°–137°; tlc $Rf_1$ 0.71, $Rf_2$ 0.85, $Rf_3$ 0.56, $Rf_4$ 0.45; UV max (MeOH) 258 mμ (t = 1800); nmr spectrum was consistent with the structure; amino acid composition: $Gly_{1.16} Tyr_{0.89} Ser_{1.0}$, $[\alpha]^{27}D$ - 8 (c 1, $CH_3CO_2H$);

Anal. Calcd for $C_{33}H_{39}N_3O_8$: C, 65.44; H, 6.49; N, 6.94. Found: C, 65.21; H, 6.39; N, 7.08.

It will be apparent from the foregoing that protective peptide acids suitable for fragment coupling in solution or on a solid support can be synthesized in good yield, using resin 7 or 7a. The Boc, Bzl, Tosyl protecting groups are stable to photolysis conditions.

The important configuration for solid phase synthesis and for clean separation by photolysis is represented by the ortho nitro benzyl group. The presence of the nitro group in the ortho position is effective to prevent loss during treatment with TFA and contributes materially to the separation of a pure derivative in high yield, without the introduction of contaminants which otherwise require removal and are difficult to remove. The carboxyl group (—COOH) on the $C_1$ position of the compounds represented by equations 2, 3, 4, 4b, 5 can be replaced by an RCOOH in which R is methyl, ethyl, propyl or other $C_1$-$C_8$ alkyl or substituted alkyl group although it is preferred to make use of a carboxyl group attached directly to the $C_1$ carbon atom.

While the invention has been described with reference to the use of polystyrene resins, other solid supports can be used such as polyamide resins, glass beads and the like to which the ortho nitro benzyl group can be attached.

It will be apparent from the foregoing examples that the protected peptide segments can be added onto the support in the form of amino amides as in

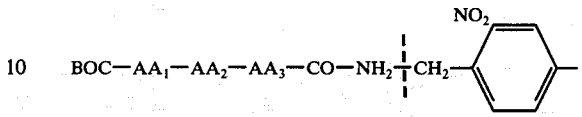

with the splitting off occurring along the broken line during photolysis, or in the form of amino acids as in

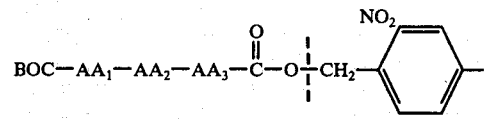

with splitting off occurring along the broken line in response to photolysis.

The ortho-nitro benzoic acid group appears to have a unique function in the described solid phase synthesis in that in addition to its ability to act as a coupling agent for joining the amino acids and/or peptides onto the resin or other support, it allows clean separation of the coupled segment or segments of amino acids and peptides in response to photolysis or activation by light.

This unique function of the ortho-nitro benzoic acid, as a coupling agent and as a release agent responsive to light, finds important utility in a number of other applications. One that appears very interesting and unique is in the field of agriculture wherein certain herbicides, fungicides, fertilizers, cytokinin compounds and the like having free hydroxyl, amino or carboxyl groups can be coupled via the ortho-nitro benzoic acid group onto a suitable solid support for subsequent application, preemergent or post-emergent, to crops, plants, grasses, trees, and the like. Slow or calculated release of the coupled component, be it a herbicide, fungicide, fertilizer, cytokinin or the like, will take place cleanly from the support in response to activation by daylight. Thus such materials can be applied in a combined or coupled form and released for availability in uncombined form over an extended period of time whereby fuller and more effective and efficient utilization can be made of such materials.

It will be apparent that a large number of other organic materials can be coupled via the ortho-nitro benzoic acid group onto a suitable support for subsequent clean and controlled release by photolysis, as in response to light.

We claim:

1. The product having the general formula

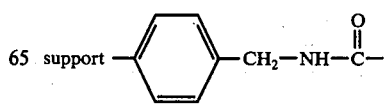

-continued

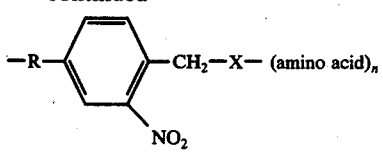

in which R is 0–8 carbon atoms in an alkyl or substituted alkyl group, X is NH, n is a number up to about 50 and the term amino acid denotes any one of the amino acids and peptides and mixtures thereof.

2. The method of producing the product having the general formula

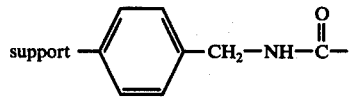

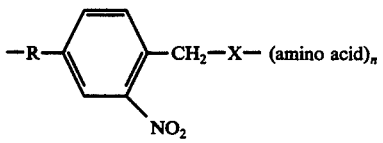

in which R is 0–8 carbon atoms in an alkyl or substituted alkyl group, X is O, n is a number up to about 50, and the term amino acid denotes any one of the amino acids and peptides and mixtures thereof, comprising the step of reacting one or more protected amino acids or peptides with the compound having the general formula

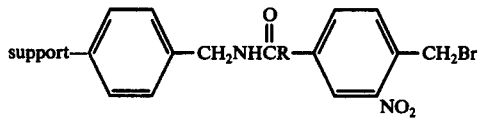

3. The method of producing the product of claim 1 comprising the step of reacting one or more protected amino acids and peptides with

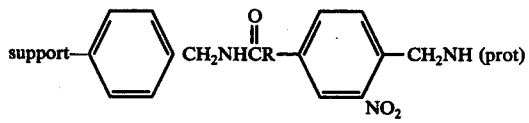

4. The method for release of fragments of peptides or amino acids from the product of claim 1 comprising subjecting the product to photolysis whereby the presence of the ortho-nitro benzyl amino group provides for clean separation of the fragments.

* * * * *

UNITED STATES PATENT OFFICE
CERTIFICATE OF CORRECTION

Patent No. 4,062,746        Dated December 13, 1977

Inventor(s) Daniel H. Rich and Sweet K. Gurwara

It is certified that error appears in the above-identified patent and that said Letters Patent are hereby corrected as shown below:

IN THE SPECIFICATION

Column 1, insert the following sentence before the first paragraph: -- The invention described herein was made in the course of work under a grant or award from the Department of Health, Education, and Welfare. --

Signed and Sealed this

Ninth Day of May 1978

[SEAL]

Attest:

RUTH C. MASON
Attesting Officer

LUTRELLE F. PARKER
Acting Commissioner of Patents and Trademarks